United States Patent [19]
Howell

[11] Patent Number: 4,661,601
[45] Date of Patent: Apr. 28, 1987

[54] RESORCINOL COMPOUNDS

[75] Inventor: Frederick H. Howell, Atherton, England

[73] Assignee: Ciba-Geigy AG, Basel, Switzerland

[21] Appl. No.: 719,184

[22] Filed: Apr. 3, 1985

Related U.S. Application Data

[63] Continuation of Ser. No. 389,993, Jun. 18, 1982, abandoned.

[30] Foreign Application Priority Data

Jun. 19, 1981 [GB] United Kingdom ............... 8119011

[51] Int. Cl.$^4$ .................. C07C 69/612; C07C 143/78; C07C 103/26; C07C 39/10
[52] U.S. Cl. ..................... 548/251; 544/170; 546/240; 548/578; 558/207; 560/70; 560/75; 560/254; 564/89; 564/170; 564/336; 564/84; 562/478; 562/476; 568/308; 568/442; 568/766; 568/763; 260/512 R; 430/473
[58] Field of Search ............... 562/476, 478; 568/766, 568/763, 308, 442; 260/465 F, 505 R, 934, 512 R; 544/170; 546/240; 548/578, 251; 558/207; 560/70, 75, 254; 564/89, 170, 336, 84

[56] References Cited

U.S. PATENT DOCUMENTS

| | | | |
|---|---|---|---|
| 2,008,337 | 7/1935 | Robinson et al. | 568/766 |
| 2,050,188 | 8/1936 | Lee et al. | 568/766 X |
| 2,051,473 | 8/1936 | Evans et al. | 568/766 X |
| 2,099,738 | 11/1937 | Ipatieff | 568/766 |
| 2,191,240 | 2/1940 | Stevens et al. | 568/766 X |
| 4,323,714 | 4/1982 | Malloy et al. | 568/766 |
| 4,484,000 | 11/1984 | Howell | 560/75 |

FOREIGN PATENT DOCUMENTS 1468342 12/1966 France ................ 560/75

OTHER PUBLICATIONS

Gopal et al., Bulletin of the Chemical Society of Japan, vol. 47 (1974) 1789-1790.

Primary Examiner—Bernard Helfin
Attorney, Agent, or Firm—Wenderoth, Lind & Ponack

[57] ABSTRACT

New compounds having the formula 1

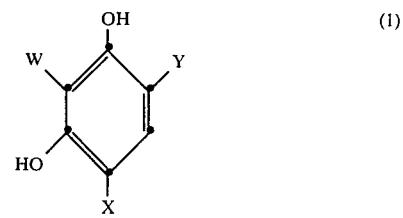

wherein W is hydrogen, halogen, n-alkyl, —NHCOR$^1$, —COR$^1$, or phenoxyacetylamino optionally substituted by one or two $C_{1-12}$ straight- or branched chain alkyl, X is a substituent in the coupling position and is selected from hydrogen, chlorine, bromine, —SR$^{11}$ or a nitrogen-containing heterocyclic residue attached at a ring nitrogen atom, and Y is a group having the formula 2

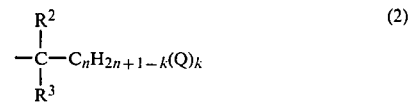

wherein Q is selected from the residues: —COOR$^4$ or —CONR$^4$R$^5$, —OM, —NR$^7$R$^8$, —PO(OR$^9$)[O]$_x$R$^{10}$ with X=0 or 1, —SO$_2$OH, —SO$_2$NR$^4$R$^5$ or CN. The groups R$^1$, R$^2$, R$^3$, R$^4$, R$^5$, R$^7$, R$^8$, R$^9$, R$^{10}$, R$^{11}$, M, k and n are defined hereinafter.

These compounds are used as black color couplers in photographic materials.

29 Claims, No Drawings

RESORCINOL COMPOUNDS

This is a continuation of application Ser. No. 389,993, filed 6/18/82, and now abandoned.

This invention relates to novel resorcinol compounds and to their production.

Resorcinols containing functional substituents directly attached to the aromatic ring are well known and are described, for instance, in Rodd's Chemistry of Carbon Compounds, 2nd Edition, Vol. III D, and in U.S. Pat. No. 4,126,461.

It has long been known that some phenolic compounds, in particular resorcinols, can be used as photographic colour couplers to yield neutral density or blackish images. However, in the past, the need to produce black images was not very great and little if any use was made of such phenolic colour couplers. Now, however, because of the very high cost of silver a great need has arisen to either replace silver as the image in silver halide sensitised photographic materials or to reinforce silver images by use of black dyes. Thus the prior art phenolic compounds have been re-examined but none of them have been found to yield black images of sufficiently good colour or density.

The subject matter of for example U.S. Pat. No. 4,126,461 relates to the use of certin resorcinol compounds as black colour couplers. However, whilst these resorcinol compounds do yield nearly acceptable black images when subjected to colour development they have been found very difficult to prepare, and the separation of non-coupling by-products therefrom has been found to be very difficult.

Two other published patent specifications which describe phenolic compounds of use as black colour couplers are British Patent Specification No. 1564349 and published British Patent Application No. 2044474. The phenolic compounds of No. 1564349 are m-aminophenol compounds. These compounds, when colour coupled in a colour development process, yield dark blue dyes which have little density below 500 n.m., which renders them virtually useless either as a final image dye or as a negative image dye used in the production of positive prints. The compounds of No. 2044474 consist of two pyrazolone nuclei linked by a 4-substituted phenol. These compounds yield a visually neutral black image when colour coupled in a colour development process, but the spectrum of their colour adsorption is very uneven and exhibits several peaks which renders them useless as negative images from which positive prints are printed.

We have found a new class of compounds, namely, resorcinols substituted by a branched chain alkyl group wherein the carbon attached to the aromatic ring is a tertiary carbon atom and which bears an alkyl group containing a functional group. These compounds when used in photographic materials overcome most of the disadvantages mentioned before.

The novel class of resorcinol compounds of the formula (1) (below), when coupled in a photographic colour development process, yield good dark black image dyes which can be used as the final dye image either alone or with a silver image in a positive print or which can be used to form a negative image from which a positive print may be obtained.

According to the present invention there is provided a compound having the formula

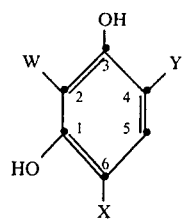

wherein

W is hydrogen, n-alkyl having from 1 to 5 carbon atoms, $-NHCOR^1$, or $-COR^1$ wherein $R^1$ is $C_{11}-C_{12}$ resp. $C_2-C_{12}$ straight- or branch chain alkyl resp. alkenyl, $C_3-C_8$ cycloalkyl, $C_7-C_{13}$ aralkyl or $C_6-C_{10}$ aryl optionally substituted by one or two $C_1-C_4$ straight- or branch chain alkyl groups, or W is phenoxyacetylamino, optionally substituted by one or two $C_{1-12}$ straight- or branched chain alkyl groups, or W is halogen;

X is a substituent in the coupling position and is selected from hydrogen, chlorine, bromine, a group of formula $-SR^{11}$ wherein $R^{11}$ is a straight- or branch alkyl having from 1 to 20 carbon atoms, aryl having from 6 to 10 carbon atoms optionally substituted by one or two $C_1-C_4$ straight- or branch chain alkyl groups, or a heterocyclic group, or X is a nitrogen-containing heterocyclic residue attached at a ring nitrogen atom;

Y is a group having the formula

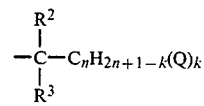

wherein Q is selected from the residues:

(a) $-COOR^4$ or $-CONR^4R^5$ wherein $R^4$ is hydrogen, straight- or branch chain alkyl having from 1 to 20 carbon atoms, optionally interrupted by 1 or more oxygen atoms, straight- or branch chain alkenyl having from 3 to 20 carbon atoms, cycloalkyl having from 3 to 12 carbon atoms, aralkyl having from 7 to 13 carbon atoms or optionally substituted $C_6-C_{10}$ aryl group and $R^5$ is hydrogen or straight- or branch chain alkyl having from 1 to 20 carbon atoms, or $R^4$ and $R^5$, together with the nitrogen atom to which they are each bonded, may form a 5- or 6-membered heterocyclic ring optionally substituted by a $C_1-C_4$ straight- or branch chain alkyl group, preferably a pyrrolidine, piperidine or morpholine ring;

(b) $-OM$ wherein M is $R^5$ or $-COR^6$ wherein $R^5$ is as defined above and $R^6$ is hydrogen, straight- or branch chain alkyl having from 1 to 20 carbon atoms, straight- or branch chain alkenyl having from 3 to 20 carbon atoms, cycloalkyl having from 3 to 12 carbon atoms, aralkyl having from 7 to 13 carbon atoms or optionally by one or two $C_1-C_4$-alkyl substituted $C_6-C_{10}$ aryl;

(c) $-NR^7R^8$ wherein $R^7$ is straight- or branch chain alkyl having from 1 to 4 carbon atoms and $R^8$ is hydrogen, straight- or branch chain alkyl having 1 to 4 carbon atoms or acyl of the formula $-COR^4$ wherein $R^4$ is as defined above or $R^7$ and $R^8$, together with the nitrogen atom to which they are each bonded, form a 5- or 6-membered heterocyclic ring optionally substituted by a $C_1-C_4$ straight- or branched chain alkyl group, preferably a pyrrolidine, piperidine, morpholine or 3,5-dimethylmorpholine ring;

(d) $-PO(OR^9)[O]_xR^{10}$ wherein x is 0 or 1, $R^9$ is hydrogen or straight- or branch chain alkyl having from 1 to 20 carbon atoms, $R^{10}$ is hydrogen or straight- or branch chain alkyl having from 1 to 20 carbon atoms when x is 1, $R^{10}$ is a straight- or branch chain alkyl group containing 1 to 5 carbon atoms if x is 0, or $R^9$ and $R^{10}$ may be linked together to form a $C_2$ or $C_3$ alkylene chain optionally substituted by one or more $C_1$-$C_{20}$ alkyl groups;

(e) $-SO_2T$ where T is $-OH$ or $-NR^4R^5$ wherein $R^4$ and $R^5$ are as defined above or (f) $-CN$;

n is an integer from 1 to 20; k is 1 or 2; $R^2$ and $R^3$ independently are straight- or branch chain alkyl having from 1 to 5 carbon atoms, and, when Q is $-CO_2R^4$, either $R^2$ or $R^3$ is optionally substituted by one or two $-CO_2R^4$ groups, or at least one of $R^2$ and $R^3$ is so linked to the residue $-C_nH_{2n+1-k}$ that there is formed a $C_5$-$C_{12}$ cycloalkylene residue substituted by $-(CO_2R^4)_k$ in which the groups $R^4$ are the same or different and wherein $R^4$ and k are as defined above; or salts thereof with acids or bases.

When k in formula (2) is 2 and Q is a residue of group (a), the two groups Q may be the same or different; likewise, when $R^2$ or $R^3$ is substituted by $-CO_2R^4$, $R^4$ therein may be the same as or different from the group $R^4$ in the residue Q.

When the groups W and/or $R^{10}$ are a $C_1$-$C_5$ straight chain alkyl group, they may be, for example, methyl, ethyl, n-propyl, n-butyl, or n-pentyl.

When the group $R^1$ is, or the phenoxyacetyl group contains, a $C_1$-$C_{12}$ straight- or branch chain alkyl it may be, for example, methyl, ethyl, n-propyl, isobutyl, n-butyl, s-butyl, t-butyl, n-pentyl, n-hexyl, n-heptyl, n-octyl, 2-ethylhexyl, 1,1,3,3-tetramethylbutyl, n-nonyl, n-decyl or n-dodecyl.

When the group $R^1$ is a $C_2$-$C_{12}$ straight- or branch chain alkenyl group it may be, for example, vinyl, prop-1-enyl, 1-methylvinyl, but-1-enyl, hexa-2,4-dienyl, undec-10-enyl or dodec-1-enyl.

When the group $R^1$ is $C_3$-$C_8$ cycloalkyl it may be, for example, cyclopropyl, cyclobutyl, cyclopentyl, cyclohexyl, cycloheptyl or cyclooctyl.

When $R^1$, $R^{11}$, $R^4$ or $R^6$ is a $C_6$-$C_{10}$ aryl group it may be for example, phenyl or naphthyl.

When the residue $R^{11}$ is a heterocyclic ring preferably a 3-7 membered ring, containing one or more oxygen, nitrogen or sulphur atoms it may be for example, oxirane, azetidine, furan, thiophene, pyrrole, oxazole, isoxazole, thiazole, isothiazole, pyrazole, imidazole, triazole, oxadiazole, thiadiazole, thiatriazole, tetrazole, pyridine, pyrimidine, pyrazine, pyridazine, triazine or azepine.

When the nitrogen containing heterocyclic residue X is a heterocyclic ring, preferably a 5-7 membered ring containing one or more nitrogen atoms, and optionally an oxygen or sulphur atom, it may be, for example, pyrrolidin-dione or piperidin-dione.

When the group $R^2$ or $R^3$ is a $C_1$-$C_5$ straight- or branched chain alkyl group it may be, for example, methyl, ethyl, n-propyl, iso-propyl, n-butyl, s-butyl, n-pentyl, or neopentyl.

When the group $R^{11}$, $R^4$, $R^5$, $R^6$, $R^9$ or $R^{10}$ is a $C_1$-$C_{20}$ straight- or branched chain alkyl group it may be, for example, methyl, ethyl, n-propyl, isopropyl, n-butyl, s-butyl, n-pentyl, n-hexyl, n-heptyl, n-octyl, 2-ethyl-hexyl, n-nonyl, n-decyl, n-dodecyl, n-tetradecyl, n-hexadecyl, n-octadecyl or n-eicosyl.

When the group $R^4$ or $R^6$ is a $C_3$-$C_{20}$ straight- or branched chain alkenyl group it may be, for example, prop-2-enyl, but-2-enyl, 3-methyl-but-2-enyl, octadec-9-enyl or eicos-2-enyl.

When the group $R^4$ or $R^6$ is a $C_3$-$C_{12}$ cycloalkyl group it may be, for example, cyclopropyl, cyclobutyl, cyclopentyl, cyclohexyl, cycloheptyl, cyclooctyl, cyclodecyl, adamantyl, or cyclododecyl.

When the group $R^1$, $R^4$ or $R^6$ is a $C_7$-$C_{13}$ aralkyl it may be for example, benzyl, phenethyl, benzhydryl, or naphthylmethyl.

When the group $R^1$, $R^{11}$, $R^4$ or $R^6$ is a $C_6$-$C_{10}$ aryl group substituted by one or two $C_1$-$C_4$ groups, or the groups $R^4$ and $R^5$, or $R^7$ and $R^8$, together with the nitrogen atom to which they are attached form a 5- or 6-membered heterocyclic ring substituted by a $C_1$-$C_4$ alkyl group, the $C_1$-$C_4$ straight- or branch chain alkyl group may be, for example, methyl, ethyl, n-propyl, iso-propyl, n-butyl, s-butyl or t-butyl.

When the group $R^7$ or $R^8$ is a $C_1$-$C_4$ straight- or branch chain alkyl group, it may be, for example, methyl, ethyl, n-propyl, iso-propyl, n-butyl or s-butyl.

When the groups $R^9$ and $R^{10}$ are linked to form a $C_2$ or $C_3$ methylene chain optionally substituted by one or more $C_1$-$C_{20}$ alkyl groups they may be for example, $-CH_2CH_2-$, $-CH_2CH_2CH_2$, $-CH_2CH(CH_3)-$, $-CH_2CH(C_2H_5)-$, $-CH_2CH(C_{20}H_{41})-$, $-CH(CH_3)CH(CH_3)-$, $-CH(CH_3)C(CH_3)_2-$, $-C(CH_3)_2C(CH_3)_2-$, $-CH_2CH_2C(CH_3)_2-$, or $-CH(CH_3)CH_2CH(CH_3)-$.

When the group $R^4$ is an optionally substituted $C_6$-$C_{10}$ aryl group, the aryl group may be substituted, independently, for example by one or two $C_1$-$C_4$ alkyl groups, or by one or two $-CF_3$, $-CN$, $-CONH_2$, $-COOCH_3$, $-NO_2$, $-OCH_3$ or halogen groups.

when the group W, or the substituent of an aryl group $R^4$ is halogen, it may be fluorine, chlorine or bromine.

Examples of salts of the compounds of the formula (1) are those formed from the alkali metals, the alkaline earth metals, transition element cations and ammonium and substituted ammonium cations. Examples of salts of the compounds of the formula (1) which contain a residue Q wherein Q is $-NR^7R^8$ are the hydrochloride, sulphate, p-toluene sulphonate, maleate and oxalate salts.

It is to be understood that the two substituents W and Y can influence the spectral absorption of the black dye of the coupled resorcinol compounds of the formula (1). However, the substituent X cannot influence the spectral absorption of the dye as this substituent leaves during the coupling reaction. However, the substituent can affect the coupling rate and sometimes increased coupling activity is obtained when X is either a chlorine or bromine atom rather than a hydrogen atom. The group $-SR^{11}$ may be a so-called development inhibiting group and sometimes it is preferred to include a D.I.R. resorcinol coupler of this type in the photographic material to caust inter- and intra-image effects such as image edge-enhancement.

Especially preferred are those compounds of the formula (1) wherein $R^2$ is methyl. In further suitable compounds of the formula (1), substituent W is hydrogen, methyl, ethyl, butyl, $-NHCOR^1$ wherein $R^1$ is $C_1$-$C_6$ resp. $C_2$-$C_6$ straight- or branch chain alkyl resp. alkenyl, cyclohexyl, benzyl, phenyl, optionally substituted by one or two methyl or ethyl groups, or W is phenoxyacetylamino optionally substituted by one or two $C_{1-12}$ straight- or branched chain alkyl groups, chlorine or bromine. Preferably, W is hydrogen, methyl, —NHCOCH$_2$C$_6$H$_5$, —NHCOC$_6$H$_5$, phenoxyacetylamino optionally substituted by one or two C$_{1-12}$ straight- or branch chain alkyl groups, chlorine or bromine.

Preferably, in compounds of the formula (1), n is 1 to 10, k is 1, R$^3$ is straight- or branch alkyl having 1 to 5 carbon atoms, Q is —CO$_2$R$^4$ or —CONR$^4$R$^5$, —OM or —NR$^7$R$^8$ wherein R$^4$, R$^5$, R$^7$, R$^8$ and M are as defined above, X is hydrogen and W is hydrogen, methyl, —NHCOCH$_2$C$_6$H$_5$, —NHCOC$_6$H$_5$, phenoxyacetylamino optionally substituted by one or two C$_{1-12}$ straight- or branched chain alkyl groups, chlorine or bromine. Preferred compounds of the formula (1) are those wherein n is 3 to 5, k is 1, R$^3$ is methyl, Q is —CO$_2$R$^4$ or —CONR$^4$R$^5$ or —NR$^7$R$^8$ wherein R$^4$, R$^5$, R$^7$ and R$^8$ are as defined above, X is hydrogen and W is hydrogen, methyl, —NHCOCH$_2$C$_6$H$_6$, —NHCOC$_6$H$_5$, phenoxyacetylamino optionally substituted by one or two C$_{1-12}$ straight- or branched chain alkyl groups The present invention also provides a process for the production of compounds of the formula (1) or salts thereof with acids or bases comprising reacting in the presence of an acid Friedel-Crafts catalyst, in the temperature range 20° to 150° C., a compound having the formula

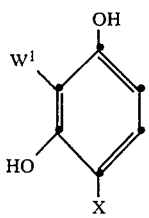

(3)

or a salt thereof, wherein X is as defined above, W$^1$ is hydrogen, n-alkyl having from 1-5 carbon atoms, —NH$_2$,—NHCOR$^1$ or —COR$^1$ wherein R$^1$ is as defined above, —NO$_2$ or halogen, with a functional alkylating agent capable of introducing a group of the formula

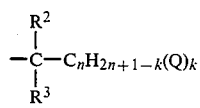

(2)

wherein R$^2$,R$^3$, Q, n and k are as defined above; optionally reducing any nitro group W$^1$ to a amino group, and then acylating this amino group to form a group —NHCOR$^1$ wherein R$^1$ is as defined above; and optionally introducing into the 2- or 6-position, substituents W and/or X which are respectively other than hydrogen, and/or optionally converting the obtained compounds into their corresponding salt with acids or bases.

The reactants of formula (3) are well known and can be produced by methods well known per se.

The ratio of the aromatic phenol (3) to alkylating species is between 10:1 and 1:1 is preferably between 5:1 and 1:1. The excess of the phenol (3) may act as a solvent.

In a further process according to the present invention, the introduction of the group —NHCOR$^1$ at the 2-position of the ring is accomplished in the following manner:

A compound of the formula

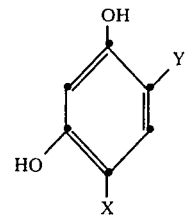

(1a)

wherein X and Y are as defined above, is nitrated with nitric acid, or other nitrating agent known to those skilled in the art of nitrating phenolic compounds, to give a compound of the formula

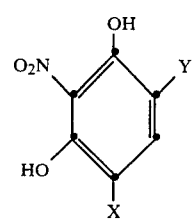

(4)

wherein X and Y are as defined above, which compound may then be reduced, using catalytic hydrogenation or other reduction process known to those skilled in the art, to give a compound of the formula

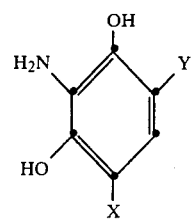

(5)

wherein Y and X are as defined above which compound may then be N-acylated with an acylating species capable of introducing the residue R$^1$CO—, for example an ester, acid halide, acid azide, acid anhydride, for examle, a mixed anhydride of the acid R$^1$COOH formed with a mono-esterified carbonic acid, pivalic acid or trichloroacetic acid, or with the free acid itself in the presence of a condensing agent, for example, a carbodiimide, to give a compound of the formula

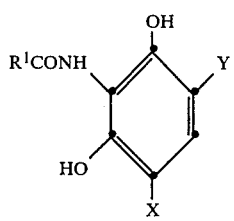

(1b)

wherein R$^1$, X and Y are as defined above. Compounds of the formula (4) and (5) suitable for reduction and/or acylation may also be obtained from compounds of the formula (3) as hereinbefore described.

In a further process according to the present invention, halogen, interhalogen or R$^{11}$S— groups may be introduced into a compound of the formula

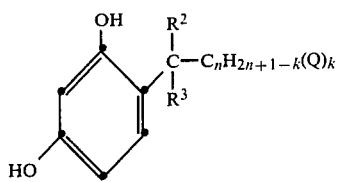
(6)

by reaction of the compounds of formula (6) with up to three mols of a halogen, interhalogen or $R^{11}$—S— compound of the formula $W^2$—Cl, or $W^2$—Br, wherein $W_2$ may be chlorine, bromine or $R^{11}S$—, to give a compound of the formula

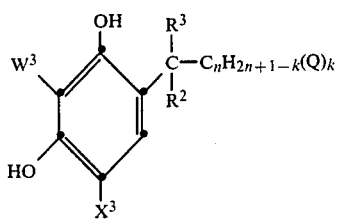
(1c)

wherein $W^3$ and $X^3$ are, independently, $W^2$ or hydrogen, providing that both $W^3$ and $X^3$ are not both hydrogen, and $R^2$, $R^3$, n, Q and k are as defined above.

Examples of reactants of the formula (3) include
resorcinol
2-acetyl resorcinol
2-methyl resorcinol
2-ethyl resorcinol
2-n-pentyl resorcinol
2-nitro-resorcinol
2-amino-resorcinol
2-acetamido-resorcinol
2-propionamido-resorcinol
2-benzamido-resorcinol
2-chloro-resorcinol
4-chloro-resorcinol
2,4-dichloro-resorcinol
2,4-dibromo-resorcinol
4-methylthio-resorcinol Functional alkylating agents which are reacted with the phenolic compound (3) contain a reactive centre, e.g. an olefinic group, or hydroxy group which is eliminated, transformed or rearranged during the course of the alkylation reaction.

Examples of functional olefins suitable for the functional alkylation of compounds of formula (3) are
methyl-5-methylhex-5-enoate,
4-carbomethoxy-1-methyl-cyclohex-1-ene,
dimethyl prenylphosphonate,
diethyl prenylphosphonate,
citronellol,
citronellyl acetate,
2-acetamido-6-methyl-5-heptene,
2-acetamido-6-methyl-6-heptene,
2-methyl-2-propene-1-sulphonic acid,
2-methyl-2-propene-1-sulphonamide,
N-methyl-2-methyl-2-propene-1-sulphonamide, or
N,N-dimethyl-2-methyl-2-propene-1-sulphonamide.

Examples of functional hydroxy compounds suitable for the functional alkylation of compounds of formula (3) are:
11-amino-undecanols selected from those having the formula:

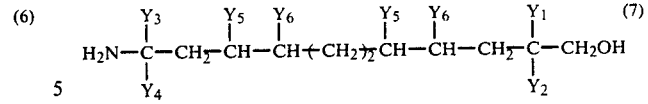
(7)

wherein $Y_1$ and $Y_3$, independently, are hydrogen or $C_1$–$C_8$ alkyl, $Y_2$ and $Y_4$, independently, are $C_1$–$C_8$ alkyl, and $Y_5$ and $Y_6$, independently, are hydrogen or $C_1$–$C_4$ alkyl and preferably
2-amino-6-hydroxy-6-methyl-heptane
2-acetamido-6-hydroxy-6-methyl-heptane
11-amino-2,2,12-trimethyl-tridecan-1-ol These 11-amino-undecanols are described in more detail, together with their method of manufacture in German Offenlegungsschrift No. 2831299.

Any group Q present in the compound of formula (1) may be converted into a different group Q, e.g. a group Q containing a carboxyl group may be converted into the corresponding esters, or a group Q containing an ester group may be transesterified to give a different ester group.

Non-limiting examples of compounds according to the present invention include:
Methyl 5-(2',4'-dihydroxyphenyl)-5-methylhexanoate
Methyl 5-(2', 4'-dihydroxy-5'-methylthio-phenyl)-5-methylhexanoate
Methyl 5-(2',4'-dihydroxy-5-n-pentylthio-phenyl)-5-methylhexanoate
Methyl 5-(2',4'-dihydroxy-5'-phenylthio-phenyl)-5-methylhexanoate
Methyl 5-[2',4'-dihydroxy-5'-(1-methyltetrazol-5-yl-thio)-phenyl]-5-methylhexanoate
Methyl 5-(3'-acetyl-2'4'-dihydroxyphenyl)-5-methyl hexanoate
Methyl 5-(2',4'-dihydroxy-5'-succinimido-phenyl)-5-methylhexanoate
Methyl 5-(2',4'-dihydroxy-3-methyl-phenyl)-5-methyl-hexanoate
Methyl 5-(2',4'-dihydroxy-3'-n-pentyl-phenyl)-5-methylhexanoate
Methyl 5-(3'-acetamido-2',4'-dihydroxyphenyl)-5-methylhexanoate
Methyl 5-(2',4'-dihydroxy-3'-n-hexanoylamino-phenyl)-5-methyl-hexanoate
Methyl 5-(2',4'-dihydroxy-3'-n-dodecanoylamino-phenyl)-5-methyl-hexanoate
Methyl 5-(3'-acrylamido-2',4'-dihydroxyphenyl)-5-methylhexanoate
Methyl 5-(3'-cyclohexylcarbonylamino-2',4'-dihydroxyphenyl)-5-methylhexanoate
Methyl 5-(3'-chloro-2',4'-dihydroxyphenyl)-5-methyl-hexanoate
Methyl 5-(3'-bromo-2',4'-dihydroxyphenyl)-5-methyl-hexanoate
Methyl5-(5'-chloro-2',4'-dihydroxyphenyl)-5-methyl-hexanoate
Methyl 5-(5'-bromo-2',4'-dihydroxyphenyl)-5-methyl-hexanoate
Methyl 5-(3',5'-dichloro-2',4'-dihydroxyphenyl)-5-methylhexanoate
Methyl 5-(3',5'-dibromo-2',4'-dihydroxyphenyl)-5-methylhexanoate
Methyl 5-(3'-benzamido-2',4'-dihydroxyphenyl)-5-methylhexanoate
2-n-Butoxy-ethyl 5-(2',4'-dihydroxy-3'-phenylacetylamino-phenyl)-5-methylhexanoate Methyl 5-[2',4'-dihydroxy-3'-(2'',4'''-di-neopentylphenoxy acetylaminophenyl)-5-methyl]hexanoate
5-(2', 4'-dihydroxyphenyl)-5-methylhexanoic acid
i-Propyl 5-(2',4'-dihydroxyphenyl)-5-methylhexanoate
n-Hexyl 5-(2',4'-dihydroxyphenyl)-5-methylhexanoate
2-Ethylhexyl 5-(2',4'-dihydroxyphenyl)-5-methylhexanoate
n-Eicosyl 5-(2',4'-dihydroxyphenyl)-5-methylhexanoate
Allyl 5-(2',4'-dihydroxyphenyl)-5-methylhexanoate
Cyclohexyl 5-(2',4'-dihydroxyphenyl)-5-methylhexanoate
Benzyl 5-(2',4'-dihydroxyphenyl)-5-methylhexanoate
Phenyl 5-(2',4'-dihydroxyphenyl)-5-methylhexanoate
p-Tolyl 5-(2',4'-dihydroxyphenyl)-5-methylhexanoate
5-(2',4'-Dihydroxyphenyl)-5-methylhexanoic acid amide
5-(2',4'-Dihydroxyphenyl)-5-methylhexanoic acid methylamide
5-(2',4'-Dihydroxyphenyl)-5-methylhexanoic acid ethylamide
5-(2',4'-Dihydroxyphenyl)-5-methylhexanoic acid n-hexylamide
5-(2',4'-Dihydroxyphenyl)-5-methylhexanoic acid n-oxtylamide
5-(2',4'-Dihydroxyphenyl)-5-methylhexanoic acid n-eicosylamide
5-(2',4'-Dihydroxyphenyl)-5-methylhexanoic acid dimethylamide
5-(2',4'-Dihydroxyphenyl)-5-methylhexanoic acid diethylamide
5-(2',4'-Dihydroxyphenyl)-5-methylhexanoic acid diallylamide
5-(2',4'-Dihydroxyhenyl)-5-methylhexanoic acid dicyclohexylamide
5-(2',4'-Dihydroxyphenyl)-5-methylhexanoic acid benzylamide
5-(2',4'-Dihydroxyphenyl)-5-methylhexanoic acid p-butyl-anilide
N-[2-(2',4'-dihydroxyphenyl)-5-methlhexanoyl]-morpholine
7-(2',4'-Dihydroxyphenyl)-3,7-dimethyl-octan-1-ol
7-(2',4'-Dihydroxyphenyl)-3,7-dimethyl-oct-1-yl acetate
7-(2',4'-Dihydroxyphenyl)-3,7-dimethyl-oct-1-yl propionate
7-(2',4'-Dihydroxyphenyl)-3,7-dimethyl-oct-1-yl n-hexanoate
7-(2',4'-Dihydroxyphenyl)-3,7-dimethyl-oct-1-yl n-eicosanate
7-(2',4'-Dihydroxyphenyl)-3,7-dimethyl-oct-1-yl crotonate
7-(2',4'-Dihydroxyphenyl)-3,7-dimethyl-oct-1-yl sorbate
7-(2',4'-Dihydroxyphenyl)-3,7-dimethyl-oct-1-yl phenylacetate
7-(2',4'-Dihydroxyphenyl)-3,7-dimethyl-oct-1-yl benzoate
7-(2',4'-Dihydroxyphenyl)-3,7-dimethyl-oct-1-yloxycarbonylcyclohexane
4-Carbmethoxy-1-(2',4'-dihydroxyphenyl)-1-methylcyclohexane
2-Amino-6-(2',4'-dihydroxyphenyl)-6-methylheptane
3-Amino-12-(2',4'-dihydroxyphenyl)-2,12-dimethyltetradecane
3-Amino-13-(2',4'-dihydroxyphenyl)-2,12-dimethyltetradecane
2-N-Methylamino-6-(2',4'-dihydroxyphenyl)-6-methylheptane
2-N-n-Butylamino-6-(2',4'-dihydroxyphenyl)-6-methylpentane
2-Dimethylamino-6-(2',4'-dihydroxyphenyl)-6-methylheptane
2-Di-N-n-butylamino-6-(2',4'-dihydroxyphenyl)-6-methylheptane
6-(2',4'-Dihydroxyphenyl)-2-morpholino-6-methylheptane
2-Acetamido-6-(2',4'-dihydroxyphenyl)-6-methylheptane
2-Hexanoylamino-6-(2',4'-dihydroxyphenyl)-6-methylheptane
2-Benzamido-6-(2',4'-dihydroxyphenyl)-6-methylheptane
1-Acetamido-5-(2',4'-dihydroxyphenyl)-5-methylhexane
3-(2',4'-Dihydroxyphenyl)-3-methyl-butane-phosphonic acid
Dimethyl 3-(2',4'-dihydroxyphenyl)-3-methyl-butane-phosphonate
Diethyl 3-(2',4'-dihydroxyphenyl)-3-methyl-butane-phosphonate
Di-2-ethylhexyl 3-(2',4'-dihydroxyphenyl)-3-methyl-butane-phosphonate
n-Dodecyl methyl 3-(2',4'-dihydroxyphenyl)-3-methyl-butane-phosphonate
2-[3-(2',4'-Dihydroxyphenyl)-3-methyl-but-1-yl]-4-methyl-1,3,2-dioxaphospholane
Ethyl 3-(2',4'-dihydroxyphenyl)-3-methyl-butane-methyl phosphinate 21-(2',4'-Dihydroxyphenyl)-21-methyl-docosanoic acid methyl ester
Methyl 5-2',4'-dihydroxyphenyl)-5,7,7-trimethyl-octanoate
Dimethyl 5-(2',4'-dihydroxyphenyl)-5-methyl-azelate
cis-4-Carbomethoxy-1-(2',4'-dihydroxyphenyl)-1-methylcyclohexane
trans-4-Carbomethoxy-1-2',4'-dihydroxyphenyl)-1-methylcyclohexane
2-(2',4'-Dihydroxyphenyl)-2-methyl-propane sulphonic acid
N-Methyl-2-(2',4'-dihydroxyphenyl)-2-methyl-propanesulphonamide
N-n-Dodecyl-2-(2',4'-dihydroxyphenyl)-2-methyl-propanesulphonamide
N-n-Eicosyl-2-(2',4'-dihydroxyphenyl)-2-methyl-propanesulphonamide
N-Allyl-2-(2',4'-dihydroxyphenyl)-2-methyl-propanesulphonamide
N-Cyclohexyl-2-(2',4'-dihydroxyphenyl)-2-methyl-propanesulphonamide
N-Benzyl-2-(2',4'-dihydroxyphenyl)-2-methyl-propanesulphonamide
N-Phenyl-2-(2',4'-dihydroxyphenyl)-2-methyl-propanesulphonamide
N,N-Dimethyl-2-(2',4'-dihydroxyphenyl)-2-methyl-propanesulphonamide
N,N-Diethyl-2-(2',4'-dihydroxyphenyl)-2-methyl-propanesulphonamide
N-[2-(2',4'-Dihydroxyphenyl)-2-methyl-propane-sulphonyl]-morpholine
1-Cyano-4-(2',4'-dihydroxyphenyl)-4-methylpentane
5-(2',4'-dihydroxyphenyl)-5-methyl azelaic acid
Diethyl 5-(2',4'-dihydroxyphenyl)-5-methyl-azelate
Di-n-propyl 5-(2',4'-dihydroxyphenyl)-5-methyl-azelate The compounds of formula I are useful in photographic silver halide materials comprising at least one silver halide emulsion layer coated on a support, there being present in the siliver halide emulsion layer(s), or in a layer in operative contact with at least one silver halide emulsion layer(s), a compound of formula I as hereinbefore defined. The photographic material which comprises in a layer thereof a compound of the formula (1) is processed after exposure by a colour development process using a primary aromatic amine colour developing agent of known type.

The support used in the photographic material of the present invention may be any one of the supports commonly used for photographic materials.

The compounds of formula I' provide a valuable means of introducing a wide variety of functional alkyl residues for optimal photographic effect. For example, the polarity of and/or ballast in the resorcinols of formula I are able to be regulated, and hence provide an effective control of solubility, compatibility, mobility-/immobility for photographic systems. Such qualities make the compounds of formula I valuable intermediates for the preparation of more complex photographically useful compounds and render them useful as black colour couplers. The following Examples further illustrate the present invention. Parts and percentages shown therein are by weight. Pressures are given in millibars.

EXAMPLE 1

110 Parts or resorcinol, 28.4 parts of methyl-5-methyl-hex-5-enoate (produced in accordance with U.S. Pat. No. 3,783,136) and 5.0 parts of the active earth Fulmont 237 ® are stirred at 125°–130° C. for 18 hours. The cooled reaction mixture is diluted with ether, filtered free of catalyst, and the ether stripped off.

The residual oil is then distilled to give 91.0 parts of a fraction $b_{10}$ up to 190° C. consisting mainly of resorcinol followed by 30 parts of a fraction $b_{0.2}$ 186°–194° C. This fraction, after dilution with petroleum ether (b.p. 40°–60° C.) containing a little ether, yields methyl-5-(2',4'-dihydroxyphenyl)-5-methylhexanoate of the formula

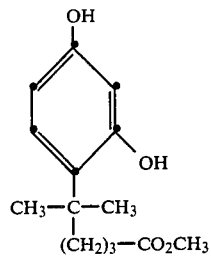

m.p. 93°–96° C., with the following percentage composition by weight:

|  | Carbon | Hydrogen |
| --- | --- | --- |
| Found | 66.34 | 8.13 |
| Calculated for $C_{14}H_{20}O_4$ | 66.65 | 7.99 |

EXAMPLE 2

In the manner described in Example 1, 55 parts of resorcinol, 15.4 parts of 4-carbomethoxy-1-methylcyclohex-1-ene (produced in accordance with Kojima et al., J. Org. Chem. 36 924 (1971)) and 5.0 parts of Fulmont 237 ® are reacted and worked up. Distillation yields 42.6 parts of recovered resorcinol followed by 15.4 parts of cis and trans-4-carbomethoxy-1-(2',4'-dihydroxyphenyl)-1-methylcyclohexane $b_{0.3}$ 218° C. with the following percentage composition by weight:

|  | Carbon | Hydrogen |
| --- | --- | --- |
| Found | 67.93 | 7.77 |
| Calculated for $C_{15}H_{20}O_4$ | 68.16 | 7.63 |

EXAMPLE 3

7-(2',4'-Dihydroxyphenyl)-3,7-dimethyloctan-1-ol, 36 parts, $b_{0.2}$ 210° C. are obtained from 73 parts of resorcinol, 52 parts citronellol, and 60 parts of Fulmont 237 ® following the procedure of Example 1, and has the following percentage composition by weight.

|  | Carbon | Hydrogen |
| --- | --- | --- |
| Found | 72.56 | 10.40 |
| Calculated for $C_{16}H_{26}O_3$ | 72.14 | 9.84 |

EXAMPLE 4

11.0 Parts of resorcinol, 10.0 parts of citronellyl acetate and 0.5 parts of p-toluene sulphonic acid are heated at 115° C. for 45 hours. The reaction mixture is then taken up in ether, washed with sodium bicarbonate solution, water, and evaporated. The residual oil is distilled and yields 3.9 parts of 7-(2',4'-dihydroxyphenyl)-3,7-dimethyloct-1-yl acetate $b_{0.2}$ 215° C. with the following percentage composition by weight:

|  | Carbon | Hydrogen |
| --- | --- | --- |
| Found | 70.44 | 9.20 |
| Calculated for $C_{18}H_{28}O_4$ | 70.09 | 9.15 |

EXAMPLE 5

(a) To 36.3 parts of 2-amino-6-hydroxy-6-methylheptane(J. Doeuvre & J. Poizat. Compt. rend. 224, 286–8 (1947)) in 100 parts of ether, is added 25.5 parts of acetic anhydride, with stirring, while keeping the temperature at 20° C.

On completion of the addition, the reaction mixture is stirred for a further 30 minutes and the volatiles removed under reduced pressure. Distillation of the residual oil yields 35.4 parts of 2-acetamido-6-hydroxy-6-methylheptane $b_{12}$ 196°–198° C. with the following percentage composition by weight:

|  | Carbon | Hydrogen | Nitrogen |
| --- | --- | --- | --- |
| Found | 63.90 | 11.71 | 7.66 |
| Calculated for $C_{10}H_{21}NO_2$ | 64.13 | 11.30 | 7.48 |

(b) 11.0 Parts of resorcinol, 7.5 parts of 2-acetamido--6-hydroxy-6-methylheptane and 0.5 parts of p-toluene sulphonic acid are sealed for 3 days at 120° C. in a glass Carius tube.

The reaction mixture, after dilution with ether, is washed with sodium bicarbonate solution, then water and evaporated. Distillation of the residual oil after a fore-run of 5.1 parts of resorcinol, yields 6.3 parts of 2-acetamido-6-(2',4'-dihydroxyphenyl)-6-methylheptane $b_{0.2}$ 234°–240° C. This fraction, after dilution with ether, crystallised to give a white solid m.p. 197°–200°

C. with the following percentage composition by weight:

|  | Carbon | Hydrogen | Nitrogen |
|---|---|---|---|
| Found | 68.59 | 9.03 | 4.95 |
| Calculated for $C_{16}H_{25}NO_3$ | 68.79 | 9.02 | 5.01 |

EXAMPLE 6

0.64 Parts of 5-mercapto-1-methyltetrazole are suspended in 17 parts of 1,1,1-trichloroethane and chlorine bubbled through this mixture until complete dissolution is obtained. The whole is evaporated to dryness under reduced pressure, treated twice with further portions of trichloroethane and evaporated to dryness. The residue is taken up in 19 parts of trichloroethane and added dropwise, under nitrogen and with protection from moisture, over 15 mins to a refluxing solution of 1.26 parts of methyl-5-(2',4'-dihydroxyphenyl)-5-methylhexanoate according to Example 1 in 19 parts of trichloroethane. The mixture is held at reflux for 8 hours, then cooled, filtered free of a small amount of solid and evaporated to dryness to give a nonvolatile oil which is purified by preparative layer chromatography (silica/1:1 ethyl acetate/cyclohexane) to give as a glass Methyl 5-[2',4'-dihydroxy-5''-(1-methyl tetrazol-5-yl-thio-phenyl]-5-methyl-hexanoate of the formula

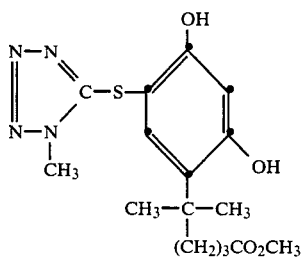

EXAMPLE 7

5.5 Parts of methyl-5-(2',4'-dihydroxyphenyl)-5-methyl-hexanoate, 50 parts of n-hexanol, and 0.5 parts of p-toluene sulphonic acid are heated on a steam-bath for 6 hours. The excess hexanol is then removed under reduced pressure and the residual oil taken up in ether, washed with sodium bicarbonate solution, water, and evaporated. Short path distillation of the residual oil at 0,7 mbar yields 5.8 parts of n-hexyl 5-(2',4'-dihydroxyphenyl)-5-methyl-hexanoate of the formula

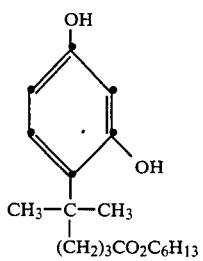

with the following percentage composition by weight:

|  | Carbon | Hydrogen |
|---|---|---|
| Found | 70.69 | 9.71 |

|  | Carbon | Hydrogen |
|---|---|---|
| Calculated for $C_{19}H_{30}O_4$ | 70.77 | 9.38 |

EXAMPLE 8

10.0 Parts of 2-methylresorcinol, 5.7 parts of 5-methyl-hex-5-enoate and 2.5 parts of Fulmont 327® are reacted together, and worked up, as described in Example 1. Distillation yields methyl 5-(2',4'-dihydroxy-3'-methylphenyl)-5-methyl-hexanoate $b_{0.7}$ 196° C. having the following percentage composition by weight.

|  | Carbon | Hydrogen |
|---|---|---|
| Found | 67.95 | 8.57 |
| Calculated for $C_{15}H_{22}O_4$ | 67.65 | 8.33 |

EXAMPLE 9

11.0 Parts of resorcinol, 12.2 parts of 2-hexanoylamino-6-hydroxy-6-methyl-heptane and 0.5 parts of p-toluene sulphonic acid are sealed for 4 days in a glass Carius tube. The reaction mixture is then poured into 500 parts of water and stirred for 30 minutes on a steam-bath. After removing the water by decantation, the above washing procedure is repeated twice again before taking up the residual oil in ether. The ether solution is then dried and stripped down under reduced pressure (16 mb) on a rotary evaporator at 100° C. to give 2-hexanoylamino-6-(2,4-dihydroxyphenyl)-6-methylheptane as an amber oil with the following percentage composition by weight

|  | Carbon | Hydrogen | Nitrogen |
|---|---|---|---|
| Found | 71.19 | 10.29 | 4.02 |
| Calculated for $C_{20}H_{33}NO_3$ | 71.60 | 9.92 | 4.18 |

EXAMPLE 10

2.5 Parts of methyl 5-(2',4'-dihydroxyphenyl)-5-methyl-hexanoate and 5.0 parts of n-octylamine are sealed into a glass Carius tube for 3 days at 120° C. The cooled reaction mixture is taken up in ether, washed first with dilute hydrochloric acid until free of the excess octylamine, and then with water. After removing the ether, the residual oil, on dilution with 40°-60° C. petroleum ether containing a little ether yields 5-(2',4'-dihydroxyphenyl)-5-methyl-hexanoic acid-n-octylamide m.p. 110°-113° C. with the following percentage composition by weight.

|  | Carbon | Hydrogen | Nitrogen |
|---|---|---|---|
| Found | 71.99 | 9.99 | 3.90 |
| Calculated for $C_{21}H_{35}NO_3$ | 72.17 | 10.09 | 4.01 |

The following compounds are prepared similarly:

(101) 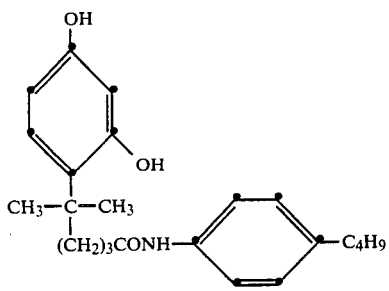

(102) 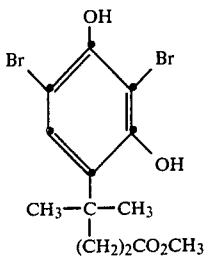

(103) 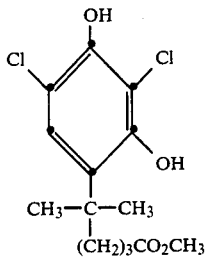

(104) 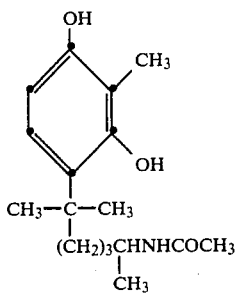

(105) 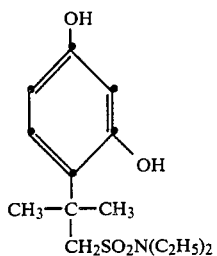

EXAMPLE 11

5.0 Parts of methyl 5-(2',4'-dihydroxyphenyl)-5-methyl-hexanoate, 50 parts of 2-ethyl-hexanol and 0.5 parts of p-toluene sulphonic acid were heated on a steam-bath for 18 hours. The reaction mixture was then diluted with ether, washed with sodium bicarbonate solution, water, and evaporated. The residue, after stripping off excess 2-ethylhexanol on a rotary evaporator at 100° C. and 0.1 mm pressure, gave 2-ethylhexyl 5-(2',4'-dihydroxyphenyl)-5-methyl-hexanoate as a viscous amber liquid with the following percentage composition by weight.

|  | Carbon | Hydrogen |
|---|---|---|
| Found | 71.94 | 9.89 |
| Calculated for $C_{21}H_{34}O_4$ | 71.96 | 9.78 |

EXAMPLE 12

Similarly prepared according to the procedure of Example 11 using n-dodecanol in place of 2-ethylhexanol, was n-dodecyl 5-(2',4'-dihydroxyphenyl)-5-methyl-hexanoate. This was obtained as a amber syrup with the following percentage composition by weight.

|  | Carbon | Hydrogen |
|---|---|---|
| Found | 74.24 | 10.38 |
| Calculated for $C_{25}H_{42}O_4$ | 73.85 | 10.41 |

EXAMPLE 13

55.0 Parts of resorcinol, 17.8 parts of dimethyl prenylphosphonate and 5.0 parts of Fulmont 237 ® were stirred at 125° C. for 18 hours. The cooled reaction mixture was then diluted with ether, filtered free of catalyst, and poured into 500 parts of water. The oil which separated out was then washed by decantation with water and extracted with ether. Following further washes with sodium bicarbonate solution and water, the ether solution after concentration yielded dimethyl 3-(2',4'-dihydroxyphenyl)-3-methyl-butane-phosphonate, m.p. 142°-3° C., with the following percentage composition by weight.

|  | Carbon | Hydrogen | Phosphorus |
|---|---|---|---|
| Found | 53.97 | 7.33 | 10.94 |
| Calculated for $C_{13}H_{21}O_5P$ | 54.16 | 7.34 | 10.75 |

EXAMPLE 14

By repeating Example 13 and using 20.6 parts of diethyl prenylphosphonate in place of the dimethylprenylphosphonate, diethyl 3-(2',4'-dihydroxyphenyl)-3-methyl-butane phosphonate monohydrate is obtained with m.p. 94°-6° C. after crystallisation from ethanol/ether.

|  | Carbon | Hydrogen | Phosphorus |
|---|---|---|---|
| Found | 53.74 | 8.21 | 9.47 |
| Calculated for $C_{15}H_{25}PO_5.H_2O$ | 53.88 | 8.14 | 9.26 |

EXAMPLE 15

5.0 parts of methyl (2',4'-dihydroxy-phenyl)-5-methylhexanoate and 10.0 parts of di-n-butylamine are sealed into a glass Carius tube and maintained at 160° C. for 48 hours. The work-up followed Example 10 to give, after a short path distillation at 0.3 mb, 5-(2',4'-dihydroxyphenyl)-5-methylhexanoic acid N,N-di-n-butylamide as a viscous amber oil with the following percentage composition by weight.

|  | Carbon | Hydrogen | Nitrogen |
|---|---|---|---|
| Found | 72.50 | 9.61 | 3.66 |
| Calculated for $C_{21}H_{35}NO_3$ | 72.17 | 10.09 | 4.01 |

EXAMPLE 14

By repeating Example 13 and using 20.6 parts of diethyl prenylphosphonate in place of the dimethyl-prenylphosphonate, diethyl 3-(2′,4′-dihydroxyphenyl)-3-methyl-butane phosphonate monohydrate is obtained with m.p. 94°-6° C. after crystallisation from ethanol/ether.

|  | Carbon | Hydrogen | Phosphorus |
|---|---|---|---|
| Found | 53.74 | 8.21 | 9.47 |
| Calculated for $C_{15}H_{25}PO_5.H_2O$ | 53.88 | 8.14 | 9.26 |

EXAMPLE 15

5.0 parts of methyl (2′,4′-dihydroxy-phenyl)-5-methylhexanoate and 10.0 parts of di-n-butylamine are sealed into a glass Carius tube and maintained at 160° C. for 48 hours. The work-up followed Example 10 to give, after a short path distillation at 0.3 mb, 5-(2′,4′-dihydroxyphenyl)-5-methylhexanoic acid N,N-di-n-butylamide as a viscous amber oil with the following percentage composition by weight.

|  | Carbon | Hydrogen | Nitrogen |
|---|---|---|---|
| Found | 72.50 | 9.61 | 3.66 |
| Calculated for $C_{21}H_{35}NO_3$ | 72.17 | 10.09 | 4.01 |

EXAMPLE 16

1.5 Parts of 2-acetyl resorcinol, 1.4 parts of methyl 5-methyl-hex-5-enoate, and 0.1 parts of p-toluene sulphonic acid are sealed into a glass Carius tube and maintained at 100° C. for 48 hours. The reaction mixture is then washed free of the acid catalyst and chromatographed through silica to yield methyl 5-(3′-acetyl-2,4-dihydroxyphenyl)-5-methyl-hexanoate with m.p. 94°-7° after crystallisation from 40°-60° C. petroleum-ether.

|  | Carbon | Hydrogen |
|---|---|---|
| Found | 65.39 | 7.30 |
| Calculated for $C_{16}H_{22}O_5$ | 65.29 | 7.53 |

EXAMPLE 17

Formulation of a resorcinol compound as an oil dispersion

A. 1 g of the resorcinol compound according to Example 1 is dissolved in 1 g isopropylated phenyl phosphate and 1 g ethyl acetate mixture, by heating under reflux; cool to 50° C.

B. 1 ml 10% (v/v in water) sulphonated PEO wetting agent and 3 ml distilled water are added to 8 g 10% (w/w in water, pH 6.5) deionised gelatin at about 50° C.

A and B are then mixed with hand stirring and are dispersed on an ultrasonic mixer for about 30 seconds.

Formulation for coating 0.45 g of the above coupler dispersion are added to 1.70 g 10% deionised gel solution and 0.54 g of a 9.2% iodide silver iodobromide emulsion.

The emulsion contains 162 g silver and 100 g gel in 1467 g total weight. Triazine hardener is added to the formulation at 20 mole/$10^5$ g gel. After adequate mixing, the coating formulation is spread by hand on to 2.4 $dm^2$ polyester (5-thou' thick) base, maintained at 40° C. during coating. Coupler and silver coating weights are approximately 25 mg/$dm^2$ with a gel coating weight of about 80 mg/$dm^2$. Coatings are dried and then incubated for about 12 hours at 45° C., 65% R.H. The coatings are overall exposed to white light for 10 seconds and processed as follows at 38° C.

Development 5 mins.
0.37 g $K_2CO_3$
1.5 ml $K_2SO_3$, 65% solution
1.05 g KBr
6.0 ml DTPA (37% solution)
2 g Hydroxylamine sulphate
1 ml $H_2SO_4$ (5N)
2.40 g CD4
1.33 g $Na_2S_2O_5$
0.94 ml Acetic acid (80% w/v)
$H_2O$ to 1 liter. pH 10.20

Bleach 6½ mins.
Ammonium bromide 150 g
Ferric ammonium EDTA 112 g
EDTA 2.5 g
Sodium nitrate 35 g
Acetic acid, glacial 10 ml
Water to 1 liter
pH 6.0±0.2

Fix 6½ mins.
Ammonium thiosulphate 130 g
Disodium EDTA 1.25 g
Sodium metabisulphite 12 g
Sodium hydroxide 2 g
pH 6.5±0.2

Wash 3 mins. 38° C.

CD4 is 4[N-ethyl-N-(2′-hydroxyethyl)amino]-2-methylaniline-hydrosulphate
EDTA is Ethylenediamine tetra-acetic acid
DTPA is Diethylenetriamine penta-acetic acid.

The adsorption spectrum shows that a very black dye is obtained which absorbs very well over the entire visible spectrum, as shown in the following table [some characteristic absorbance values ($\epsilon$) at the corresponding wavelengths (in nm)].

| Wavelength (nm) | Absorption ($\epsilon$) |
|---|---|
| 345 | 1,5 |
| 350 | 1,35 |
| 400 | 0,95 |
| 450 | 0,98 |
| 480 | 1,02 |
| 500 | 0,98 |
| 550 | 0,82 |
| 600 | 0,72 |
| 650 | 0,63 |
| 700 | 0,53 |

I claim:
1. Compounds having the formula

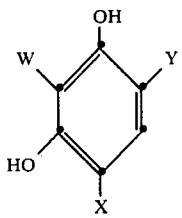

wherein
W is hydrogen, methyl, —NHCOR¹ wherein R¹ is phenyl or benzyl or W is phenoxyacetylamino or W is halogen; X is selected from hydrogen, chlorine or bromine, Y is a group having the formula

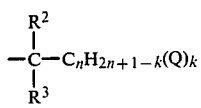

wherein Q is selected from the residues:
(a) —COOR⁴ or —CONR⁴R⁵ wherein R⁴ is hydrogen, straight- or branch chain alkyl having from 1 to 20 carbon atoms, optionally interrupted by 1 or more oxygen atoms, straight- or branch chain alkenyl having from 3 to 20 carbon atoms, cycloalkyl having from 3 to 12 carbon atoms, aralkyl having from 7 to 13 carbon atoms or optionally substituted $C_6$–$C_{10}$ aryl group and, R⁵ is hydrogen or straight- or branch chain alkyl having from 1 to 20 carbon atoms, or R⁴ and R⁵, together with the nitrogen atom to which they are each bonded, may form a 5- or 6-membered heterocyclic ring containing nitrogen as the sole hetero atom optionally substituted by a $C_1$–$C_4$ straight- or branch chain alkyl group,
(b) —OM wherein M is R⁵ or —COR⁶ wherein R⁵ is as defined above and R⁶ is hydrogen, straight- or branch chain alkyl having from 1 to 20 carbon atoms, straight- or branch chain alkenyl having from 3 to 20 carbon atoms, cycloalkyl having from 3 to 12 carbon atoms, aralkyl having from 7 to 13 carbon atoms or optionally by one or two $C_1$–$C_4$-alkyl substituted $C_6$–$C_{10}$ aryl;
(c) —NR⁷R⁸ wherein R⁷ is hydrogen or straight- or branch chain alkyl having from 1 to 4 carbon atoms and R⁸ is hydrogen, straight- or branch chain alkyl having 1 to 4 carbon atoms or acyl of the formula —COR⁴ wherein R⁴ is as defined above or R⁷ and R⁸, together with the nitrogen atom to which they are each bonded, form a 5- or 6-membered heterocyclic ring optionally substituted by a $C_1$–$C_4$ straight-, or branched chain alkyl group,
(d) —PO(OR⁹)$_x$R¹⁰ wherein x is 1, R⁹ is hydrogen, methyl or ethyl, R¹⁰ is methyl or ethyl; or
(e) —SO₂T where T is —OH or —NR⁴R⁵ wherein R⁴ and R⁵ are as defined above; n is an integer from 1 to 10; k is 1; R² is methyl and R³ is straight- or branch chain alkyl having from 1 to 5 carbon atoms, or salts thereof with acids or bases.

2. Compounds according to claim 1 wherein R³ is straight- or branch alkyl having 1 to 5 carbon atoms, Q is —CO₂R⁴ or —CONR⁴R⁵, —OM or —NR⁷R⁸, X is hydrogen and W is hydrogen, chlorine, bromine, methyl, —NHCOCH₂C₆H₅ or —NHCOC₆H₅, wherein R⁴, R⁵, R⁷, R⁸ and M are as defined in claim 1.

3. Compounds according to claim 1 wherein n is 3 to 5, k is 1, R² and R³ are methyl and Q is —COOR⁴ or —CONR⁴R⁵ or —NR⁷R⁸, wherein R⁴, R⁵, R⁷ and R⁸ are as defined in claim 1, and W is hydrogen, methyl, —NHCOCH₂C₆H₅, —NHCOC₆H₅, or phenoxyacetylamino.

4. A compound of claim 1 which is 4-carbomethoxy-1-(2',4'-dihydroxyphenyl)-1-methylcyclohexane.

5. A compound of claim 1 which is 7-(2'-4'-Dihydroxyphenyl)-3,7-dimethyloctan-1-ol.

6. A compound of claim 1 which is 7-(2',4'-dihydroxyphenyl)-3,7-dimethyloct-1-yl acetate.

7. A compound of claim 1 which is 2-acetamido-6-(2',4'-dihydroxyphenyl)-6-methylheptane.

8. A compound of claim 1 is methyl 5-[2',4'-dihydroxy-5'-(1''-methyl-tetrazol-5''-yl-thio)-phenyl]-5-methyl-hexanoate.

9. A compound of claim 1 which is n-hexyl 5-(2',4'-dihydroxyphenyl)-5-methyl-hexanoate.

10. A compound of claim 1 which is methyl 5-(2'-4'-dihydroxy-3'-methylphenyl)-5-methyl-hexanoate.

11. A compound of claim 1 which is 2-hexanoylamino-6-(2',4'-dihydroxyphenyl)-6-methylheptane.

12. A compound of claim 1 which is 5-(2',4'-dihydroxyphenyl)-5-methyl-hexanoic acid-n-octylamide.

13. A compound of claim 1 which is 5-(2'-4'-dihydroxyphenyl)-5-methyl-hexanoic acid p-butylphenylamide.

14. A compound of claim 1 which is methyl 5-(3',5'-dibromo-2',4'-dihydroxyphenyl)-4-methyl-pentanoate.

15. A compound of claim 1 which is methyl 5-(3',5'-dichloro-2',4'-dihydroxyphenyl)-5-methyl-hexanoate.

16. A compound of claim 1 which is 2-acetamido-6-(2',4'-dihydroxy-3'-methyl-phenyl)-6-methylheptane.

17. A compound of claim 1 which is 1-diethylaminosulfonyl-2-(2',4'-dihydroxyphenyl)-2-methylpropane.

18. A compound of claim 1 which is 2-ethylhexyl 5-(2',4'-dihydroxyphenyl)-5-methyl-hexanoate.

19. A compound of claim 1 which is n-dodecyl 5-(2',4'-dihydroxyphenyl)-5-methyl-hexanoate.

20. A compound of claim 1 which is dimethyl 3-(2',4'-dihydroxyphenyl)-3-methyl-butane-phosphonate.

21. A compound of claim 1 which is diethyl 3-(2',4'-dihydroxyphenyl)-3-methyl-butane phosphonate monohydrate.

22. A compound of claim 1 which is 5-(2',4'-dihydroxyphenyl)-5-methylhexanoic acid N,N-di-n-butylamide.

23. A compound of claim 1 which is methyl 5-(3'acetyl-2',4-dihydroxyphenyl)-5-methyl-hexanoate.

24. Compounds having the formula

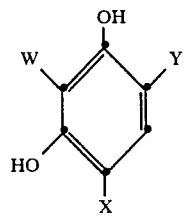

wherein

W is hydrogen, methyl, —NHCOR$^1$ wherein R$^1$ is phenyl or benzyl or W is halogen, and X and Y are as defined in claim 1.

25. Compounds according to claim 1 wherein W is hydrogen, methyl, —NHCOR$^1$ wherein R$^1$ is phenyl or benzyl or W is phenoxyacetylamino, or W is chlorine or bromine.

26. A compound of claim 1 which is methyl 5-(2'4'-dihydroxyphenyl)-5-methyl hexanoate.

27. A compound of claim 1 where the 5- or 6-membered heterocyclic ring is a pyrrolidine ring formed by R$_4$ and R$_5$ together with the nitrogen to which they are each bonded.

28. A compound of claim 1 wherein the 5- or 6-membered heterocyclic ring is a piperidine ring formed by R$_4$ and R$_5$ together with the nitrogen to which they are each bonded.

29. A compound of claim 1 wherein the 5- or 6-membered heterocyclic ring is a morpholine ring formed by R$_4$ and R$_5$ together with the nitrogen to which they are each bonded.

* * * * *